United States Patent [19]

Yamada et al.

[11] Patent Number: 5,089,411
[45] Date of Patent: Feb. 18, 1992

[54] METHOD OF CULTURING A STRAIN OF RHODOCOCCUS RHODOCHROUS HAVING NITRILE HYDRATASE ACTIVITY

[75] Inventors: Hideaki Yamada; Toru Nagasawa, both of Kyoto, Japan

[73] Assignees: Hideaki Yamada, Kyoto; Nitto Kagaku Kogyo Kabushiki Kaisha, Tokyo, both of Japan

[21] Appl. No.: 417,259

[22] Filed: Oct. 5, 1989

[30] Foreign Application Priority Data

Oct. 6, 1988 [JP] Japan .................. 63-252645
Feb. 28, 1989 [JP] Japan .................. 64-046818

[51] Int. Cl.$^5$ .................. C12N 1/38; C12N 1/20; C12P 13/02
[52] U.S. Cl. .................. 435/244; 435/129; 435/252.1
[58] Field of Search .................. 435/129, 244, 252.1

[56] References Cited

U.S. PATENT DOCUMENTS 4,629,700 12/1986 Prevatt et al. .................. 435/128

OTHER PUBLICATIONS

Nagasawa et al., Biochemical and Biophysical Research Communications, vol. 155, No. 2, 1988, pp. 1008–1016.

Primary Examiner—Douglas W. Robinson
Assistant Examiner—Carol Geckle
Attorney, Agent, or Firm—Emmanuel J. Lobato; Robert E. Burns

[57] ABSTRACT

Cells of bacteria of the species *Rhodococcus rhodochrous* having a high nitrile hydratase activity can be obtained in a high yield by adding to a culture medium at least one of urea and its derivatives and cobalt ion in the preparation of cells of bacteria having nitrile hydratase activity by cultivating *Rhodococcus rhodochrous* bacteria capable of producing nitrile hydratase.

2 Claims, No Drawings

METHOD OF CULTURING A STRAIN OF RHODOCOCCUS RHODOCHROUS HAVING NITRILE HYDRATASE ACTIVITY

BACKGROUND OF THE INVENTION

The present invention relates to a method of producing in a high yield cells of a microorganism of the species *Rhodococcus rhodochrous* having a high nitrile hydratase activity.

In recent years, there have been increasing attempts to utilize microorganisms and enzymes as they are or in immobilized state as catalysts for various single or complex chemical reactions.

Nitrile hydratase has been found by Hideaki Yamada, one of the present inventors, et al. as an enzyme capable of hydrating nitriles to produce the corresponding amides. (Reference: Agric. Biol. Chem. 46 1165 (1982)) As one example of the utilization of this enzyme, a method for preparation of amides from nitriles in the presence of bacteria having nitrile hydratase has been proposed. (References: Japanese Patent Pub. No. 37951/1984 and U.S. Pat. No. 4,637,982)

Further, we have proposed a method for preparation of amides, especially suitable for preparation of amides from aromatic nitriles. (References: Japanese Patent Appln. No. 231744/1988 and U.S. Pat. application Ser. No. 243,986) Under this situation, a method that can ensure the production of cells of *Rhodococcus rhodochrous* bacteria having a high nitrile hydratase activity in high yield would be remarkably beneficial.

SUMMARY OF THE INVENTION

An object of the present invention is to solve the above problem by adding specific substances, i.e., urea or its specific derivative and cobalt ion, to a culture medium in the cultivation of the bacteria.

Thus, the method for cultivation of bacteria of the species *Rhodococcus rhodochrous* having a high nitrile hydratase activity according to this invention comprises adding to a culture medium at least one of urea and urea derivatives of the following formulae [I] to [III]:

$$R_1R_2NCONR_3R_4 \qquad [I]$$

wherein $R_1$, $R_2$, $R_3$ and $R_4$ each are —H, —CH$_3$ or -C$_2$H$_5$, all the substituents not being —H;

$$R_5R_6NCOOC_2H_5 \qquad [II]$$

wherein $R_5$ and $R_6$ each are —H, —CH$_3$ or —C$_2$H$_5$; and $$NH_2CSNH_2 \qquad [III]$$

and cobalt ion in the preparation of cells of bacteria having nitrile hydratase activity by cultivating *Rhodococcus rhodochrous* bacteria capable of producing nitrile hydratase.

The addition of at least one of urea and specific urea derivatives of formulae [I] to [III] and cobalt ion to the culture medium during the cultivation of *Rhodococcus rhodochrous* bacteria remarkably increases the nitrile hydratase activity per unit culture fluid.

This increase in nitrile hydratase activity per unit culture fluid is presumably traceable to the increase in cell concentration (i.e., yield) and/or cell activity (i.e., quantity of the nitrile hydratase in the cells).

In the present invention, the addition of urea or a derivative thereof and cobalt ion is especially effective in increasing the cell activity.

DETAILED DESCRIPTION OF THE INVENTION

I. *Rhodococcus rhodochrous* bacteria

The bacteria used in the present invention are *Rhodococcus rhodochrous* bacteria having nitrile hydratase activity and the capability of hydrating nitriles, particularly, even aromatic nitriles, to produce the corresponding amides. A specific example of such bacteria is *Rhodococcus rhodochrous*, strain J-1 (FERM BP-1478), disclosed in Japanese Patent Appln. No. 231744/1988 and U.S. Pat. application Ser. No. 243,986 mentioned earlier. The details of the strain J-1 are given in these patent applications as follows.

1. Origin and Deposition

The strain J-1 was isolated by us from the soil in Sakyo-ku, Kyoto, Japan, and deposited on Sept. 18, 1987 with the Fermentation Research Institute, Agency of Industrial Science and Technology, Ministry of International Trade and Industry of Japan, where it was assigned the accession number FERM BP-1478 under the Budapest Treaty.

2. Bacteriological Characteristics (a) Morphological Characteristics
 (1) Shape and size of cell: 0.9–1.0 $\mu \times$ 3–10 $\mu$
 (2) Polymorphism: An elongated rod-shaped cell in the initial stage of cultivation grows to form a straight stick with snapping, and then is divided into short bacillus form.
 (3) Motility: Immotile
 (4) Formation of spores: None
 (5) Grain staining: Positive
 (6) Acid-fast property: Negative
 (7) Heterophile granulocyte: Observed
(b) Cultural Characteristics on Various Culture Media (30° C.)
 (1) Bouillon-agar plate culture: Circle with 1-mm diameter (48 hours), irregular, smooth, rather dry on the surface, flat, opaque, and pale orange-pink.
 (2) Bouillon-agar slant culture: Filament with a smooth surface and a slightly convex, rather dry cross section, and pale orange-pink.
 (3) Bouillon liquid culture: Abundant growth formation of membrane. The culture fluid becomes fairly turbid and a precipitate is formed as the cell grows.
 (4) Bouillon-gelation stab culture: Good growth on the surface in the shape of a funnel along the stabbed area, but scant growth in the undersurface. Gelatin is not liquefied.
 (5) Litmus-milk: No change.
(c) Physiological properties
 (1) Reduction of nitrate: Positive
 (2) Denitrification: Negative
 (3) MR Test: Negative
 (4) VP Test: Negative
 (5) Formation of indole: Positive
 (6) Formation of hydrogen sulfide: Positive
 (7) Hydrolysis of starch: Negative
 (8) Utilization of citric acid:
  Kocur's culture medium: Negative
  Christensen's culture medium: Positive (9) Utilization of inorganic nitrogen source:
  Nitrate: Positive
  Ammonium salt: Positive
(10) Formation of pigments: Negative
(11) Urease: Positive
(12) Oxidase: Negative
(13) Catalase: Positive
(14) Hydrolysis of cellulose: Negative
(15) Growth range: pH: 5–10
  Temp.: 10°–41° C.
(16) Behavior toward oxygen: Aerobic
(17) Decomposition of tyrosine: Positive
(18) Decomposition of adenine: Positive
(19) Phosphatase: Positive
(20) Hydrolysis of Tween 80: Positive
(21) O-F Test: 0 (weak)
Heat resistance (in 10% skim milk at 72° C. for 15 min.): None
(23) Formation of acid & gas from saccharide:

|  | Acid | Gas |
| --- | --- | --- |
| L-Arabinose | − | − |
| D-Xylose | − | − |
| D-Glucose | + | − |
| D-Mannose | − | − |
| D-Fructose | + | − |
| Maltose | + | − |
| Sucrose | + | − |
| Lactose | − | − |
| Trehalose | − | − |
| D-Sorbitol | + | − |
| D-Mannitol | + | − |
| Glycerol | + | − |

(24) Growth in a single carbon source:

| Inositol | − |
| --- | --- |
| Maltose | + |
| D-Mannitol | + |
| Rhamnose | − |
| D-Sorbitol | + |
| m-Hydroxybenzoic acid | + |
| Sodium adipate | + |
| Sodium benzoate | + |
| Sodium citrate | + |
| Sodium lactate | + |
| Testotetrone | + |
| L-Tyrosine | + |
| Glycerol (1%) (w/v) | (+) |
| Trehalose | (+) |
| p-Hydroxybenzoic acid (1%) (w/v) | + |

(+): slightly positive

(25) Analysis of fatty acid & cell wall: The cell contains unsaturated and saturated straight-chain fatty acids and tuberculostearic acid. TLC of mycolic acid gives a single spot.

According to the characterization of the above listed bacteriological properties in the light of Bergy's Manual of Systematic Bacteriology (1986), the strain J-1 is an aerobic, Gram-positive, weakly acid-fast, catalase-positive and non-endospore forming bacillus with no flagellum. This strain is in the shape of an elongated bacillus and a mycelium in the initial stage of growth, grows with branching and then is divided into short bacillus form. In view of these features, the strain J-1 is considered to fall under Nocardia type bacteria.

The analysis of the fatty acid composition has revealed that the bacterium contains unsaturated and saturated straight-chain fatty acids including tuberculostearic acid. Since the TLC of mycolic acid gives a single spot having the same Rf value as the standard bacterium *Rhodococcus rhodochrous* (IFO 3338), the bacterium is distinguished from those of the genus Mycobacterium. This bacterium is also distinguished from Nocardia bacteria in view of the composition (number of carbon atoms) of the mycolic acid.

As a result of investigation of other biochemical properties, this bacterium has been identified as *Rhodococcus rhodochrous*.

II. Urea and its derivatives

In the present invention, urea and urea derivatives of the formulae [I] to [III] shown hereinbefore function as enzyme inducers, but, from what we have heretofore known, i.e., typical enzyme inducers are nitriles or amides, inter alia, crotonamide, it is wholly unexpected that urea and its derivatives can effectively induce nitrile hydratase. Surprisingly, urea and its derivatives, when used singly and not in combination with other enzyme inducers, exhibit far higher efficacy than conventional enzyme inducers. Furthermore, since urea is less expensive than other enzyme inducers, the method of the present invention can be advantageously applied to industry from economy viewpoint.

Examples of the compounds of the formula [I] among the urea derivatives used in the present invention are methylurea, ethylurea, 1,1-dimethylurea, and 1,3-dimethylurea.

Exemplary compounds of the formula [II] are urethane and methylurethane.

The compound of the formula [III] is thiourea.

Urea or its derivatives are added to the culture medium in one batch at one time or sequentially. The term "sequentially" as used herein is intended to mean both "continuously" and "incrementally".

III. Cobalt ion

Nitrile hydratase cannot be obtained simply by adding urea or its derivatives to the culture medium, and it is essential in the present invention that cobalt ion be added to the culture medium. (Although there is zero nitrile hydratase activity in an iron ion containing culture medium, the activity will be developed in a culture medium which contains cobalt ion and the presence of cobalt ion is essential for the production of nitrile hydratase by the bacterium of the present invention as has been set forth in Japanese Patent Appln. No. 231744/1988 and U.S. Pat. No. 243,986 mentioned earlier.)

Ordinarily, cobalt ion is formed by adding a water-soluble cobalt compound to the culture medium which is aqueous. The water-soluble cobalt compounds are as defined in chemical encyclopedias, so that it may be easy for those skilled in the art to suitably select and use one of such compounds.

Typical examples of the cobalt compounds are those which afford $Co++$ or $Co+++$, particularly $Co++$, such as cobalt chloride, cobalt sulfate, cobalt acetate, cobalt bromide and cobalt borate.

Additionally, vitamin $B_{12}$ and metallic cobalt can also be used as cobalt sources. Vitamin $B_{12}$ contains cobalt in the form of a complex which is ionized by autoclave treatment, while metallic cobalt is ionized by the oxidizing function of microorganisms during cultivation.

IV. Cultivation/Production of nitrile hydratase

The *Rhodococcus rhodochrous* bacteria of the present invention can be cultivated under any conditions suitable for the purpose except that urea or its derivatives and cobalt ion are added to the culture medium.

For example, predetermined amounts of urea or its derivatives and cobalt ion are added to basal media listed below, and cultivation may be carried out at a temperature of about 15° to 50° C., preferably about 20° to 45° C., and more preferably about 30° C. at a pH of 7 to 9 for about 30 hours or longer, preferably for 40 hours or longer (up to, for example, 120 hours).

The overall concentration of the urea or its derivatives in the culture medium is about 1 to 30 g/l, preferably about 2 to 20 g/l, and more preferably about 5 to 15 g/l, while the concentration of the cobalt ion is about 5 to 15 mg/l as calculated in terms of $CoCl_2$.

| Basal medium: | |
|---|---|
| Component | Amount (in 1 l of the medium) |
| Culture medium A | |
| $K_2HPO_4$ | 13.4 g |
| $KH_2PO_4$ | 6.5 g |
| NaCl | 1.0 g |
| $MgSO_4.7H_2O$ | 0.2 g |
| Vitamin mixture* | 0.1 ml |
| Distilled water | Balance (pH 7.0) |
| *Composition (in 1 l of the solution): | |
| Biotin | 2.0 μg |
| Calcium pantothenate | 0.4 mg |
| Inositol | 2.0 mg |
| Nicotinic acid | 0.4 mg |
| Thiamin hydrochloride | 0.4 mg |
| Pyridoxine hydrochloride | 0.4 mg |
| p-Aminobenzoic acid | 0.2 ng |
| Riboflavin | 0.2 mg |
| Folic acid | 0.01 ng |
| Distilled water | Balance |
| Culture medium B | |
| $K_2HPO_4$ | 0.5 g |
| $KH_2PO_4$ | 0.5 g |
| $MgSO_4.7H_2O$ | 0.5 g |
| Yeast extract | 3.0 g |
| Distilled water | Balance (pH 7.2) |
| Culture medium C | |
| Glucose | 10 g |
| $K_2HPO_4$ | 0.5 g |
| $KH_2PO_4$ | 0.5 g |
| $MgSO_4.7H_2O$ | 0.5 g |
| Yeast extract | 1.0 g |
| Peptone | 7.5 g |
| Distilled water | Balance (pH 7.2) |

V. Experimental Examples

Measurement and Definition of Enzyme Activity (1) Method for Measuring Nitrile Hydratase Activity The nitrile hydratase activity was determined as follows.

2 ml of a reaction solution comprising 1.0 ml of benzonitrile (20 mM), 1.0 ml of 3-cyanopyridine (1 M) or 1.0 ml of acrylonitrile (1 M) as a substrate; 0.5 ml of potassium phosphate buffer (0.1 M, pH 7.0); and a predetermined amount of bacterium cells (isolated from a culture fluid) was caused to react at 20° C for a predetermined time period, and the reaction was then terminated with the addition of 0.2 ml of 1N HCl.

(2) Definition of Nitrile Hydratase Activity

The activity was determined for the specific activity (S.A.) and the total activity (T.A.) as defined below.

S.A.: μmole product amide/mg-cells/min.

T.A.: μmole product amide/ml-culture medium/min.

REFERENCE EXAMPLE 1

The J-1 strain was cultured using a culture medium, the composition of which is specified below, under culturing conditions which are also specified below, and the expression of the nitrile hydratase activity is examined by adding $CoCl_2$ and/or $FeSO_4$ to the culture medium during culture.

| (i) Composition of the culture medium | |
|---|---|
| Ingredient | Amount (in 1 liter of medium) |
| Vitamin mixture | 3.0 ml |
| $K_2HPO_4$ | 0.5 g |
| $KH_2PO_4$ | 0.5 g |
| $MgSO_47H_2O$ | 0.5 g |
| Propionitrile | 2 ml |
| Distilled water | Balance (pH 7.2) |
| (ii) Culture condition | |
| 28° C./70–80 hours | |

The results obtained are shown below.

It can be seen that the nitrile hydratse activity is not developed even if $FeSO_4$ is added to the basic medium; nitrile hydratase activity is developed when $CoCl_2$ is added, and the addition of $FeSO_4$ to the system to which $CoCl_2$ has been added will adversely affect the results.

REFERENCE TABLE 1

| Metal ion added | | | | | | | | | | |
|---|---|---|---|---|---|---|---|---|---|---|
| $CoCl_2$ (mg) | 0 | 0 | 0 | 0 | 0 | 10 | 10 | 10 | 10 | 10 |
| $FeSO_4$ (mg) | 0 | 5 | 10 | 20 | 40 | 0 | 5 | 10 | 20 | 40 |
| Amount of cells*1 (mg/ml) | 1.06 | 1.14 | 1.25 | 1.24 | 1.34 | 2.04 | 1.90 | 2.16 | 2.16 | 2.07 |
| Enzyme activity | | | | | | | | | | |
| U/mg of cells*2 | 0 | 0 | 0 | 0 | 0 | 0.59 | 0.26 | 0.34 | 0.32 | 0.16 |
| U/ml of medium | 0 | 0 | 0 | 0 | 0 | 1.20 | 0.49 | 0.73 | 0.69 | 0.33 |

*1 Amount of cells based on dry weight
*2 U: Unit of activity, wherein one unit (U) of nitrile hydratase activity is defined as the amount of an enzyme required for producing benzamide from benzonitrile, measured by carrying out the reaction with 2 ml of a reaction mixture which contains 10 mM of benzonitrile, 30 mM of potassium phosphate buffer (pH 7.0) and certain amount of the cells of a microorganism (isolated from a culture medium) at 10° C. for 5 minutes and adding 2 ml of 1N-HCl to stop the reaction; the am ount of cells are based on the dry weight.

EXAMPLE 1

Predetermined amounts of urea were each added to the above basal medium C containing 10 mg/l of $CoCl_2$. To 60 ml each of the resulting culture medium was added 4 ml of a preculture fluid of *Rhodococcus rhodochrous*, strain J-1 (FERM BP-1478) (obtained using the basal medium C), and shake culture was carried out at 28° C. for 96 hours.

For comparison purposes, culture was conducted similarly in a medium containing either urea or CoCl₂ alone.

The results obtained are summarized in TABLE 1.

From the TABLE, it will be noted that the addition of both urea and CoCl₂ is essential for increased production of nitrile hydratase.

Example 2

Strain J-1 was subjected to culture similarly as in Example 1 at 28° C. for 48 to 120 hours in the basal medium C mentioned above in the presence of 10 mg/l of CoCl₂, while adding or not adding predetermined amounts of enzyme inducers (urea and crotonamide) as set forth in TABLE 2.

Presented in TABLE 2 are T.A. and S.A. values obtained when the maximum T.A. values were marked during the measurements of the activity.

As is apparent from the TABLE, the use of urea alone as an enzyme inducer contributes effectively toward increasing production of nitrile hydratase.

TABLE 1

| CoCl₂ (mg/l) | Urea (g/l) | Cell Concentration (mg/ml) | Benzonitrile T.A. | S.A. | 3-Cyanopyridine T.A. | S.A. | Acrylonitrile T.A. | S.A. |
|---|---|---|---|---|---|---|---|---|
| 0 | 0 | 4.61 | 0.11 | 0.02 | 0.75 | 0.16 | 3.59 | 0.70 |
| 0 | 7.5 | 5.53 | 0.11 | 0.02 | 1.00 | 0.18 | 4.31 | 0.78 |
| 10 | 0 | 5.28 | 1.09 | 0.21 | 3.70 | 0.70 | 17.7 | 3.35 |
| 10 | 2.0 | 5.17 | 25.2 | 4.87 | 39.6 | 7.66 | 189 | 36.5 |
| 10 | 5.0 | 5.03 | 65.6 | 13.0 | 162 | 32.2 | 774 | 154 |
| 10 | 7.5 | 4.99 | 210 | 42.1 | 519 | 104 | 2480 | 497 |
| 10 | 10 | 4.72 | 186 | 39.4 | 471 | 99.7 | 2250 | 477 |
| 10 | 15 | 4.26 | 191 | 44.9 | 515 | 121 | 2460 | 578 |
| 10 | 20 | 3.96 | 162 | 40.9 | 363 | 91.7 | 1740 | 438 |

TABLE 2

| Culture Medium | CoCl₂ (mg/l) | Urea (g/l) | Crotonamide (g/l) | Benzonitrile T.A. | S.A. |
|---|---|---|---|---|---|
| C | 10 | — | 2.0 | 23.2 | 6.0 |
| C | 10 | — | 4.0 | 24.6 | 6.1 |
| C | 10 | — | 7.5 | 16.6 | 5.8 |
| C | 10 | 5.0 | 2.0 | 32.6 | 6.5 |
| C | 10 | 7.5 | — | 213 | 42.2 |

EXAMPLE 3

Predetermined amounts of urea derivatives were each added to the above basal medium C containing 10 mg/l of CoCl₂. To 60 ml each of the resulting culture medium was added 4 ml of a preculture fluid of *Rhodococcus rhodochrous*, strain J-1 (FERM BP-1478) (obtained using the basal medium C), and shake culture was carried out at 28° C. for 96 hours.

For comparison purposes, culture was conducted similarly in a medium containing methylurea alone or CoCl₂ alone.

The results are shown in TABLE 3 in which are presented T.A. and S.A. values obtained when the maximum T.A. values were marked during the measurements of the activity. In this TABLE are added for reference the results obtained for 7.5 g/l of urea.

As is apparent from the TABLE, the use of both a urea derivative and CoCl₂ is essential for increased production of nitrile hydratase.

TABLE 3

| CoCl₂ (mg/l) | Enzyme Inducer | Amount of Enzyme Inducer (g/l) | Cell Concentration (mg/ml) | 3-Cyanopyridine T.A. | S.A. |
|---|---|---|---|---|---|
| 0 | Methylurea | 7.5 | 4.78 | 0 | 0 |
| 10 | — | 0 | 4.94 | 3.20 | 0.65 |
| 10 | Methylurea | 7.5 | 5.72 | 230 | 40.2 |
| 10 | Ethylurea | 7.5 | 5.76 | 245 | 42.5 |
| 10 | 1,1-Dimethylurea | 7.5 | 6.44 | 150 | 23.3 |
| 10 | 1,3-Dimethylurea | 7.5 | 4.16 | 104 | 25.0 |
| 10 | Methylurethane | 7.5 | 6.19 | 166 | 26.8 |
| 10 | Thiourea | 7.5 | 1.99 | 40.2 | 20.2 |
| 10 | Urea | 7.5 | 4.99 | 519 | 104 |

We claim:

1. A method of culturing the strain *Rhodococcus rhodochrous* J-1 (Ferm BP-1478) comprising cultivating *Rhodococcus rhodochrous* strain J-1 in a culture medium essentially free of crotonamide and essentially free of iron ions and during the cultivation adding to said culture medium cobalt ion in a concentration of 5 to 15 mg/l calculated as CoCl₂, and at least one compound selected from urea and a urea derivative of the following formulae I, II and III:

$$R_1R_2NCONR_3R_4 \qquad \text{I}$$

wherein R₁, R₂, R₃ and R₄ are each —H, —CH₃ or —C₂H₅, except that all substitutents are not —H;

$$R_5R_6NCOOC_2H_5 \qquad \text{II}$$

wherein R₅ and R₆ are each —H, —CH₃ or —C₂H₅ and $$NH_2CSNH_2 \qquad \text{III}$$

wherein the overall concentration in the culture medium of urea or a urea derivative of formulae I to III is 1-30 g/l in order to prepare cells of bacteria having nitrile hydratase activity.

2. A method as claimed in claim 1, wherein urea is added to the culture medium.

* * * * *